United States Patent

Novak

[11] Patent Number: 5,985,936
[45] Date of Patent: Nov. 16, 1999

[54] METHOD OF PREVENTING AND DELAYING ONSET OF ALZHEIMER'S DISEASE AND COMPOSITION THEREFOR

[75] Inventor: Egon Novak, Richmond, Canada

[73] Assignee: Forbes Medi-Tech, Inc., Vancouver, Canada

[21] Appl. No.: 08/993,901

[22] Filed: Dec. 18, 1997

[51] Int. Cl.⁶ .................................................. A61K 31/045

[52] U.S. Cl. ........................................... 514/724; 514/729

[58] Field of Search ....................................... 514/724, 729

[56] References Cited

U.S. PATENT DOCUMENTS 5,589,182  12/1996  Tashiro et al. ........................... 424/423
5,770,749   6/1998  Kutney et al. ............................ 552/545

*Primary Examiner*—Raymond Henley, III
*Attorney, Agent, or Firm*—Townsend and Townsend and Crew LLP

[57] ABSTRACT

A method of preventing and/or delaying the onset of Alzheimer's disease in an animal comprises administering to the animal a phytosterol composition. A composition useful for preventing and/or delaying the onset of Alzheimer's disease in an animal comprises a phytosterol composition.

4 Claims, No Drawings

METHOD OF PREVENTING AND DELAYING ONSET OF ALZHEIMER'S DISEASE AND COMPOSITION THEREFOR

FIELD OF THE INVENTION

This invention relates to the field of Alzheimer's disease and to methods of prevention therefor and delaying the onset thereof.

BACKGROUND OF THE INVENTION

Alzheimer's disease ("AD") is an immutably progressing dementing disorder. It's major pathologic hallmark is the development of cytoskeletal changes in a few susceptible neuronal cells. These changes do not occur inevitably with advancing age, but once the disease has begun, spontaneous recovery or remissions are not observed.

The initial cortical changes, described further below, develop in poorly myelinated transentorhinal region of the medial temporal lobe. The destructive process then follows a predictable pattern as it extends into other cortical areas. Location of the tangle-bearing neurons and the severity of the changes allow the distinction of six stages in disease progression from stages I–II which are clinically silent to stages V–VI which mark fully developed AD. A relatively small number of patients display particularly early changes, indicating that advanced age is not a prerequisite for the evolution of the lesions. Accordingly AD is thus an age-related but not an age-dependent disease.

There are a number of current theories as to the cause and mechanism of AD progression, many associated with genetic defects. A very small percentage of AD patients have a defect on chromosome 21 relating to the gene for the production of amyloid precursor protein ("APP"). APP is a large protein involved in cell growth and repair, which, when cleaved into the small indigestible protein beta-amyloid ("B-A"), can accumulate in plaques within the brain.

Further interesting studies have focused on the relationship between late-onset familial AD and a polymorphic gene on chromosome 19 encoding for apolipoprotein-E ("apo-E"), a 34,000 molecular weight protein involved in movement of cholesterol and other lipids in and out of cells throughout the body. The role of apo-E in lipid transport and metabolism is critical and is discussed further below. The neurobiological role of apo-E has been borne from a number of observations over the years. Firstly, apo-E mRNA is abundant in the brain, where it is synthesized and secreted primarily by astrocytes (Elshourbagy et al. 1985). Secondly, apo-E containing lipoproteins are found in the cerebrospinal fluid and appear to play a major role in lipid transport in the central nervous system (Pitas et al. 1987). Thirdly, apo-E plus a source of cholesterol promotes marked neurite extension in dorsal root ganglion cells in culture (Handelmann et al. 1992). Fourthly, apo-E levels dramatically increase after peripheral nerve injury (Muller et al. 1985). Accordingly, apo-E appears to participate both in the scavenging of lipids generated after axon degeneration and in the redistribution of these lipids to sprouting neurites for axon regeneration and later to Schwann cells for remyelination of the new axons (Boyles et al. 1989).

The implication of a role for apo-E, which exists in three different isoforms encoded by three separate allelles (E-2, E-3, E-4) that are inherited in a co-dominant fashion at a single genetic locus, in the pathogenesis of AD specifically stems from the association of apo-E with the two characteristic neuropathologic lesions of AD-extracellular neuritic plaques (representing deposits of B-A) and intracellular neurofibrillary tangles (representing filaments of a microtubule-associated protein called tau). For a review, please refer to Weisgraber et al. 1994).

In particular, there has been found a genetic association between the apo-E4 isoform and AD. E4 homozygous individuals display a greater risk of developing AD than E4 heterozygotes, who in turn, display a greater risk than individuals with no E4 allelle. Although the precise mechanism by which this correlation exists remains elusive, researchers have provided some possible answers. It may involve a biological effect of the protein produced by this allelle, analogous to manner by which the decrease in the avidity of the binding of apo-E2 to the LDL receptor results in an increase in plasma cholesterol levels in E2 homozygotes. Strittmatter et al (1993) demonstrated that apo-E4 binds more effectively to the B-A peptide leading to the enhanced formation of senile plaques as compared to other two isoforms and have thereby proposed that it is not the presence of apo-E4, but the lack of the other apo-E isoforms that results in the increased predisposition to AD (Strittmatter et al. 1994a), Similarly, with respect to the isoform-specific interaction of apo-E with tau protein, whose phosphorylated forms are the major constituent of neurofibrillary tangles, apo-E3 but not E4 has been shown to bind with tau with high avidity (Strittmatter et al. 1994a). This differential effect has led to the hypothesis that the apo-E3 normally allows tau protein to stabilize microtubules and that its decrease or absence in patients with one or two apo-E4 allelles leads to a dissociation of tau from microtubules and its enhanced phosphorylation and polymerization into the pathological paired helical filaments (Strittmatter et al. 1994b).

Despite the enormous research in the area of AD progression, treatments are scarce and methods of prevention and/or delaying the onset of this debilitating illness are virtually non-existent.

It is an object of the present invention to obviate or mitigate the above disadvantages.

SUMMARY OF THE INVENTION

The present invention provides a method of preventing and/or delaying the onset of Alzheimer's disease ("AD") in animals which comprises administering to the animal a phytosterol composition.

Further, the present invention provides compositions which are effective in preventing or delaying the onset of AD which compris

PREFERRED EMBODIMENTS OF THE INVENTION

Phytosterols are sterol-like compounds synthesized in plants with no direct nutritional value to humans. In plants, they are required for cell function in a manner similar to the way in which cholesterol is required in humans. The average Western diet contains up to 360 mg of phytosterols per day. Recently, these dietary plant sterols have received a great deal of attention because of their possible anti-cancer properties and their ability to reduce cholesterol levels when fed to a number of mammalian species, including humans. Heretofore, plant sterols have never been suggested or investigated in the prevention and delayed onset (treatment) of AD.

Chemically, phytosterols closely resemble cholesterol in structure. The major phytosterols are beta-sitosterol, campesterol and stigmasterol. Others include stigmastanol (beta-sitstanol), desmosterol, chalinasterol, poriferasterol, clionasterol, and brassicasterol.

Although phytosterols are available in vegetable oils and in vegetables, the amounts are not necessarily in significant enough concentrations or in the correct form to confer the advantages of the present invention. What is provided within the scope of the present invention is a method of preventing and/or delaying the onset of AD by administering to animals, specifically humans, a phytosterol composition. This composition can be incorporated directly into food supplements, oils, vitamins and therapeutic formulations as required and described further below.

It is contemplated that the phytosterol compositions of the present invention may be admixed with generally available food items for wide-spread distribution to the population, regardless of genetic pre-disposition to AD. Alternatively, these compositions may be selectively administered on a more vigorous program targeting those individuals who are at risk for developing particular forms of AD i.e. familial AD. In a preferred form, the compositions are admixed with a vegetable oil selected from the group comprising safflower oil, sesame seed oil, corn oil, rice bran oil, olive oil and rape seed oil. Supplementing olive oil is the most preferred as the oil is widely used and is low in phytosterols and polyunsaturated fatty acids. Alternatively, the compositions may be incorporated into saturated fat (lard) based products or shortenings such as butter or margarine.

In another embodiment, the compositions may be incorporated into formulations with other conventional or herbal products for the prevention or therapy of AD. These products include, but are not limited to, cholinesterase inhibitors such as Aricept™, risperidone (the schizophrenia medicine now found to be helpful in controlling AD-related aggression), and possible memory-enhancing herbal remedies such as ginkgo.

The basis of the present invention is the use of phytosterols generally in preventing and/or delaying the onset of AD. Although preferred compositions to achieve this end are listed below, they are by no means to be interpreted as limiting the broad scope of the present invention as many phytosterols, alone or in various combinations may achieve the same beneficial results.

The preferred phytosterol compositions of the present application comprise beta-sitosterol, campesterol, stigmastanol and optionally, campestanol, and analogs/derivatives thereof. In one embodiment, the composition of the present invention comprises at least 10% campesterol and no more than 75% beta-sitosterol. In another preferred form, the composition comprises from 10–25% campesterol, 10–25% stigmastanol and from 45–75% beta-sitosterol. Optionally, from 2–6%, more preferable 3% campestanol may be present.

In another preferred form, the compositions of the present invention comprise the following ratio of phytosterols: beta-sitosterol (1); campesterol (0.2–0.4) and stigmastanol (0.2–0.5). More preferably, campesterol and stigmastanol together represent at least 50% of the total concentration of beta-sitosterol. The compositions of the present invention include the following ratios of the three key plant sterols:

| beta-sitosterol | campesterol | stigmastanol |
|---|---|---|
| 1 | 0.354 | 0.414 |
| 1 | 0.330 | 0.203 |
| 1 | 0.268 | 0.299 |

Other preferred compositions have been found to have plant sterol distributions (in %) as follows:

| beta-sitosterol | campesterol | stigmastanol |
|---|---|---|
| 62.6 | 16.6 | 23.2 |
| 64.7 | 16.4 | 17.2 |
| 60.0 | 13.6 | 16.3 |

It is to be understood, however, that in any of these preferred compositions, other plant sterols may be present. Similarly adjuvants or carriers may form part of the composition as required. Depending on the mode of deivery of the compositions of the rpesent invention, the dosage may be somewhat varied. It is most preferred that approximately 1.0 g to 3.0 g be administered daily.

In the method of the present invention, AD is prevented and/or the onset delayed by the administration to the individual of the phytosterol compositions described in detail above. The exact mechanism by which learning ability and memory are enhanced, age-dependent synapse loss is reduced, and neurodegenerative processes are slowed by dietary phytosterol administration is unclear, although the applicants do have several theories which are outlined in more detail below. These theories are not intended to limit the scope of the present invention, but conversely, serve to show the complexity of phytosterols in animal lipid homeostasis.

As discussed in the background to the invention above, the apo-e4 phenotype has been shown in humans to represent an important risk factor in AD. There is also some evidence showing the relationship between AD and cardiovascular disease (Kalaria, 1997). An overview of the function of apo-E is provided below, along with information tying in apo-E to the present invention, with a view to understanding the proposed mechanisms of action of the phytosterols.

APO-E

Apo-E is just one of the lipid carrier molecules referred to as apolipoproteins. These proteins have three main functions. Firstly, they help solubilize highly hydrophobic cholesterol and triglycerides by interacting with phospholipids (the core of the complex is the lipid, the outer shell is the apolipoprotein) to enable these lipids to be transported. Secondly, apolipoproteins regulate the reaction of lipids with enzymes such as lipoprotein lipase and lecithin:cholesterol acyltransferase. Thirdly, the apolipoproteins bind to cell surface receptors and thus determine the sites of uptake and rates of degradation of other lipoprotein constituents, notably cholesterol.

Apo-E is unique among lipoproteins in that it has a special relevance to nervous tissue. During development or after injury in the peripheral nervous system, apo-E co-ordinates the mobilization and redistribution of cholesterol in repair, growth and maintenance of myelin and neuronal membranes (Boyles et al. 1989, supra). In the central nervous system, much less is known about the function of apo-E, which makes the finding apo-E4 being a possible marker for AD (discussed in the background section above) all the more intriguing.

APO-E MICE

Several human and animal studies have shown the cholesterol lowering effects of plant sterols, including the anti-atherogenic effects of phytosterols compositions in Apo-E deficient mice (PCT Patent Application PCT/CA95/00555 published Apr. 4, 1996 and incorporated herein by reference and Moghadasian et al. 1996). More recently, apo-E deficient mice have been shown to be a suitable animal model to study the pathophysiology of AD. Since in apo-E deficient mice, phytosterols prevent atypical cholesterol distribution (skin, tendons, aorta and principal arteries) phytosterols could have an important role in determining cholesterol tissue distribution, even in brain cells, independent apo-E phenotypes (study in progress by applicant).

CHYLOMICRON REMNANTS

Chylomicrons are the largest lipoprotein particles consisting mainly of triglyceride with smaller amounts of phospholipid, free cholesterol and esters. They are synthesized in the intestine or enterocytes in response to dietary fat and cholesterol, enter the mesenteric and thoracic duct lymph where they acquire apo-E. The enzyme lipoprotein lipase ("LL") catalyses the hydrolysis of the triglyceride of the chylomicrons wherein the free fatty acids generated are taken up primarily by adipocytes and the remaining smaller portions of the lipoprotein (which are enriched in cholesterol) are referred to as chylomicron remnants ("CR"). CR are rapidly cleared from the plasma by a selective liver apo-E dependent receptor mechanism (low density lipoprotein related receptor the "LRP receptor"), where the cholesterol is either used in membrane or lipoprotein biosynthesis or excreted as free cholesterol or metabolised to bile acids. For particles to be internalized, the presence of apo-E is considered critical. The liver and the brain cells are particularly rich in this LRP receptor.

VERY LOW DENSITY LIPOPROTEINS

Very low density lipoprotein ("VLDL") is similar in structure to chylomicrons but is smaller and contains less triglyceride but relatively more cholesterol, phospholipid and protein (mix of apo-E, apo-C and apo-B100). VLDL is synthesized mainly in the liver and its chief function is the carriage of triglycerides. VLDL particles vary in size but subsequent lipolysis by either LL or hepatic lipase ("HL") produces even smaller particles: VLDL remnants (also known as intermediate density lipoprotein) and low density lipoproteins ("LDL").

LIPOPROTEIN LIPASES

There are at least two distinct triglyceride lipases. Extra-hepatic or lipoprotein lipase ("LL") is found mainly in adipose tissue and skeletal muscle. Hepatic lipase ("HL") is located on the endothelium of liver cells. Both LL and HL are involved in the catabolism of CR and VLDL.

APO-E RECEPTORS

There are four known receptors that are involved in apo-E/lipoprotein (chylomicron, VLDL, or LDL) transport into cells from plasma: the low density lipoprotein receptor ("LDL receptor"), the LRP receptor (defined above), the newly described very low density lipoprotein receptor ("VLDL receptor") and the epithelial glycoprotein 330 receptor ("GP330 receptor"). All four receptors are found in the brain. The discovery that the receptor for the activated form of alpha2-macroglobulin ("alpha2/M") is identical to the LRP receptor is evidence that the LRP receptor is a multi-factorial receptor protein called alpha2M/LRP receptor. This receptor is expressed in nearly every cell in the body, particularly the liver and the brain, targets enzymes, proteins, CR and LDL cholesterol and seems to play a complex role in proteolysis, immunity, cell proliferation and cell death.

With respect to the transport of apo-E into neuronal cells, it has been found not only that neurons are very rich in surface LRP receptors and that LRP receptor immunoreactivity was increased in plaques in AD (Rebeck et al. 1993) but that apo-E/LRP complexes are also localized to plaques in the human brain (Ikeda et al, unpublished data). LRP not only binds apo-E-containing remnants but also interacts with important enzymes of chylomicron metabolism such as LL. This latter binding is independent of apo-E (Beisiegel et al. 1991). Noteworthy is the ability of phytosterols to prevent, in apo-E deficient mice, the development of atherosclerctic plaque formation.

Within the liver, CR are catabolized by LL or an apo-E-dependent receptor mechanism, namely the LRP or alpha2M/LRP receptor.

PROPOSED MECHANISMS OF ACTION OF PHYTOSTEROLS ON AD

There are three inter-related primary mechanisms by which phytoserols exert a beneficial effect on AD prevention and onset:

1) phytosterols increase apo-E independent CR clearance in the liver via hepatic LRP by a complex (and not yet fully understood) mechanism involving allosteric LL activation and LL complex formation with CR; and/or 2) phytosterols decrease the circulation of and/or the apo-E dependent receptor-mediated uptake of apo-E/lipoprotein complexes into cells generally but brain cells in particular; and/or 3) phytosterols decrease endothelial cell shedding and preserve the blood-brain barrier endothelial function.

Phytosterols are bound to circulating chylomicrons and lipoproteins and have a modifying effect on these particles within plasma and on the physicochemical properties of enzymes such as LL and HL. In other words, the applicants suggest that phytosterols function as apoproteins thereby changing the structure, composition and function of circulating chylomicrons and lipoproteins and in addition, influence many other critical cellular functions indirectly through the LRP receptor.

Simply put, with respect to the first mechanism, phytosterols bind to lipoproteins i.e. chylomicrons, and prevent the binding of these particles to the alpha2M/LPR receptors and subsequent passage of these particles across the cellular barrier into the brain. Accordingly, the amount of apo-E in neuronal cells would be reduced which is particularly important for those individuals who are apo-E4 homozygotes.

In addition, phytosterols increase the activity of LL through allosteric modification so that phytosterol-enriched chylomicrons are rapidly metabolized by this enzyme. The CR are then rapidly cleared from the circulation by apo-E independent hepatocyte CR receptors which are identical to LRP receptors. As discussed above LL is a major enzyme involved in triglyceride (chylomicron and VLDL) metabolism having a carboxyl ("C") and a nitrogen ("N") terminal. Its' regulation, structural and functional relationship and C-terminal lipoprotein lipase domain (in induction of CR catabolism via the LRP receptor) are fairly well understood by researchers and it focused the applicants on the possibility of an apo-E independent lipoprotein catabolism.

It is believed that the phytosterol compositions of the present invention alter the physico-chemical properties of lipoproteins by allosteric modification. Consequently, the LL activity, influenced by the phytosterols, could more efficiently utilize enzyme mass for triglyceride catabolism by the "N" terminal catalytic site, whereas the "C" terminal domain could serve as a ligand for CR. The "C" LL domain-CR complexes with low fatty acid hepatic flux, are then internalized by a receptor identical with the scavenger receptors (alpha2M/LRP) and then catabolized by hepatic lipase with marked further degradation of the CR fatty acid esters.

In other words, it is possible that phytosterols enhance LL "C" terminal ligand binding to CR thereby increasing CR catabolism. Since these processes are independent of apo-E, they should not result in LDL receptor up-regulation.

With respect to the third but complementary mechanism, that phytoserols decrease cell shedding (the endothelial effect) it has been found by the applicants that in normal and hypercholesterolemic rats, dietary administration of a phytosterol composition decreased endothelial cell shedding by 50–70% respectively. This is a critical finding considering the role of endothelium in the blood-brain barrier and in the passage of unwanted damaging particles into the brain which may lead to AD. Furthermore, integrins, a diverse class of glycoprotein receptors are involved in cell extracellular matrix ("ECM") interaction. The disruption of integrin expression in the brain may be associated with an increase in apo-E sub-endothelial penetrance. The ECM directs the growth, differentiation and function of the overlying epithelium (Getlenburg et al. 1990).

Furthermore, the applicants believe that plant sterols modify membranes, including the blood-brain barrier. Accordingly, transportation of potentially toxic substances such as beta-amyloid precursor across this membrane may be impaired resulting in the delayed onset of AD.

In addition, apo-E deficient mice suffer from oxidative stress in their brains (Mathews et al. 1996). This could be associated with AD. The applicants have shown in current on-going research that plant sterols may have anti-oxidant acitivity. Accordingly, these sterols may protect the brain from oxidative stress leading to a delay in onset or even prevention of AD.

A summary of possible modes of action of phytosterols is as follows:
1) Enzymatic effect
  allosteric modification of LL and molecular configuration changes in lipoprotein complexes
2) Chylomicrons and CR
  stimulation of LL→LL-enriched CR
  inhibition HL
  CR→VLDL or LRP receptor non-apo-E dependent uptake utilizing C-terminal of LL monomer as ligand for receptor binding and/or internalization, HL monomer inhibition of uptake of CR through LDL receptor
  entering smooth hepatocyte endoplasmic reticulum
  stimulation of 7-alpha-hydroxylase→increase in bile acid synthesis
  increasing cholesterol bile output, decreasing liver cholesterol content, increasing HMG-CoA activity in a manner independent of LDL metabolism i.e. VLDL OR LDL receptor could be inhibited by CR
  decreased shedding endothelial cells
  formation of more hydrophilic membranes

REFERENCES

1. ELSHOURBAGY et al. 1985 Apolipoprotein E mRNA is abundant in the brain and adrenals, as well as in the liver, and is present in other peripheral tissues in rats and marmosets. *Proc Natl. Acad. Sci. USA* 82:203–207
2. PITAS et al. 1987 Lipoproteins and their receptors in the CNS:Characterization of lipoproteins in CSF and identification of apolipoproteins B,E (LDL) in brain. *J. Biol. Chem.* 262:14352–14360
3. HANDELMANN et al. 1992 Effects of apolipoprotein E, Beta-very low density lipoproteins and cholesterol on the extension of neurites by rabbit dorsal root ganglion neurons in vivo. *J. Lipid Res.* 33:1677–1688
4. MULLER et al. 1985 A specific 37,000-dalton protein that accumulates in regenerating but not in non-regenerating mammalian nerves. *Science* 228:499–501
5. BOYLES et al. 1989 A role for apolipoprotein-E, apolipoprotein A-I and low density lipoprotein receptors in cholesterol transport during regeneration and remyelination of the rat sciatic nerve. *J. Clin. Invest.* 83:1015–1031
6. WEISGRABER et al. 1994 Lipoproteins, neurobiology, and Alzheimer's disease: Structure and function of apolipoprotein-E. *Curr. Opin. Struct. Biol.* 4:507–515
7. STRITTMATTER et al. 1993 Binding of human apolipoprotein-E to synthetic amyloid beta-peptide: isoform specific effects and implications for late onset Alzheimer's disease. *Proc. Natl. Acad. Sci. USA* 90:8098–8102
8. STRITTMATTER et al. 1994a Isoform specific interactions of apolipoprotein-E with microtubule associated protein tau. implications for Alzheimer's disease. *Proc. Natl. Acad. Sci. USA* 91:11183–11186
9. STRITTMATTER et al. 1994b Hypothesis: microtubule instability and paired helical filament formation in the Alzheimer's disease brain are related to apolipoprotein-E genotype. *Exp. Neurol.* 125:163–171
10. KALARIA et al. 1997 *Society Neurosci.* 23:2215
11. MOGHADASIAN et al. 1996 *Arteriosclero. Throm. Vasc. Biol.* 17: 119–126
12. REBECK et al. 1993 Apolipoprotein E in sporadic Alzheimer's disease: allelic variation and receptor interactions. *Neuron* 11(4):575–580
13. BEISIEGEL et al. 1991 Lipoprotein lipase enhances the binding of chylomicrons to low density lipoprotein receptor related protein. *Proc. Natl. Acad. Sci. USA* 88:8342–8346
14. GETLENBURG et al. 1990 The tissue matrix:cell dynamic and hormone action. *Endocrine Review* 11:399
15. MATHEWS et al. 1996 *Brain Res.* 718:181–184

We claim:

1. A method of preventing Alzheimer's disease in an animal which comprises administering to the animal a phytosterol composition which comprises beta-sitosterol, campesterol and stigmastanol.

2. The method of claim 1 wherein campesterol and stigmastanol together comprise at least 50% of the concentration of beta-sitosterol.

3. The method of claim 1 wherein the composition comprises from 10–25% campetserol, 10–25% stigmastanol and from 45–75% beta-sitosterol.

4. The method of claim 1 wherein the composition additionally comprises campestanol.

* * * * *